United States Patent
Gretz et al.

(10) Patent No.: US 12,186,221 B2
(45) Date of Patent: Jan. 7, 2025

(54) BLUE LIGHT PHOTOBIOMODULATION

(71) Applicants: Urgo Recherche Innovation et Developpement, Chenove (FR); Blue Light Photobiomodulation GDBR, Mannheim (DE)

(72) Inventors: Norbert Gretz, Mannheim (DE); Fabiola Arpino, Mannheim (DE); Anja Becker, Mannheim (DE); Anna Klapczynski, Mannheim (DE); Natalia Kuch, Mannheim (DE); Marielle Bouschbacher, Chambolle-Musigny (FR); Julien Steinbrunn, Messigny et Vantoux (FR)

(73) Assignees: Urgo Recherche Innovation et Developpement, Chenove (FR); Blue Light Photobiomodulation GDBR, Mannheim (DE)

( * ) Notice: Subject to any disclaimer, the term of this patent is extended or adjusted under 35 U.S.C. 154(b) by 470 days.

(21) Appl. No.: 17/095,900

(22) Filed: Nov. 12, 2020

(65) Prior Publication Data
US 2021/0059848 A1    Mar. 4, 2021

Related U.S. Application Data (62) Division of application No. 16/321,355, filed as application No. PCT/EP2017/068951 on Jul. 27, 2017, now abandoned.

(51) Int. Cl.
*A61F 13/0246* (2024.01)
*A61F 5/01* (2006.01)
(Continued)

(52) U.S. Cl.
CPC ........... *A61F 5/0123* (2013.01); *A61F 5/01* (2013.01); *A61F 13/0246* (2013.01);
(Continued)

(58) Field of Classification Search
CPC ............. A61F 13/0246; A61N 5/0616; A61N 2005/0645; A61N 2005/0663; C12N 5/0629; C12N 5/0656; A61B 2017/00884
See application file for complete search history.

(56) References Cited

U.S. PATENT DOCUMENTS

2005/0177093 A1* 8/2005 Barry ................. A61N 5/0616
604/20
2013/0103123 A1  4/2013 Khan et al.
(Continued)

FOREIGN PATENT DOCUMENTS

| CN | 205339869 U | * | 6/2016 | |
| TW | 201325652 A | * | 7/2013 | ........... A61N 5/0616 |

OTHER PUBLICATIONS

"Tan et al., Optical Wound Therapeutic Apparatus, Jun. 29, 2016, translated CN 205339869 U" (Year: 2016).*

*Primary Examiner* — Carl H Layno
*Assistant Examiner* — Aya Ziad Bakkar
(74) *Attorney, Agent, or Firm* — Maier & Maier, PLLC (57) ABSTRACT

The invention is directed to a light source device comprising a light emitting element for emitting a blue light having a wavelength ranging from 435 to 500 nm, the light source device being configured to provide the blue light to at least one cell at a transmitted fluence ranging from 0.01 to 18. J/cm$^2$ to promote or induce growth and proliferation of the cell and wherein the light emitting element has a power density ranging from 0.05 to 30 mW/cm$^2$. The invention is also directed to a light source assembly comprising a product adapted to be in contact with the skin or a wound and a light source device connected to the product for providing blue light to at least one skin cell, preferably of the wound.

14 Claims, 2 Drawing Sheets

(51) Int. Cl.

| | |
|---|---|
| *A61N 5/06* | (2006.01) |
| *B29C 33/38* | (2006.01) |
| *C12N 5/071* | (2010.01) |
| *C12N 5/077* | (2010.01) |
| *G05B 19/4099* | (2006.01) |
| *G06T 7/30* | (2017.01) |
| *A61F 2/50* | (2006.01) |
| *B29L 31/00* | (2006.01) |

(52) U.S. Cl.
CPC ........ *A61N 5/0616* (2013.01); *B29C 33/3835* (2013.01); *C12N 5/0629* (2013.01); *C12N 5/0656* (2013.01); *G05B 19/4099* (2013.01); *G06T 7/30* (2017.01); *A61F 2002/505* (2013.01); *A61F 2002/5053* (2013.01); *A61F 5/0125* (2013.01); *A61N 2005/0645* (2013.01); *A61N 2005/0663* (2013.01); *B29L 2031/757* (2013.01); *G05B 2219/35134* (2013.01); *G05B 2219/49007* (2013.01); *G06T 2207/30052* (2013.01)

(56) References Cited

U.S. PATENT DOCUMENTS

| | | |
|---|---|---|
| 2014/0277293 A1 | 9/2014 | Jagdeo et al. |
| 2016/0016001 A1* | 1/2016 | Loupis ................. H05B 45/20 604/20 |
| 2016/0030765 A1 | 2/2016 | Towne et al. |

\* cited by examiner

BLUE LIGHT PHOTOBIOMODULATION

TECHNICAL FIELD

This invention relates to a light source device able to promote or induce growth and proliferation of skin cells, notably for the treatment of wounds and injuries, through a photobiomodulation mean. The invention also relates to a light source assembly comprising such a light source device.

BACKGROUND OF THE INVENTION

Healing of a wound is a natural physiopathological process, the human and animal tissues being able to repair lesions by specific processes of reparation and regeneration.

Natural healing of a wound proceeds mainly according to three major chronological sequences. Each one of these sequences is characterized by specific cellular activities and is controlled by a multiplicity of signals of regulation (as well as positive and negative) which, collectively, orchestrate and frame the progression of the process of repair. One distinguishes as follows:
  the inflammatory phase;
  the phase of proliferation (which includes the phase of granulation and epithelialization; and
  the phase of remodeling.

The first phase, also called the inflammatory phase, begins since the rupture from the blood-vessels, event which starts the formation of a clot (coagulation of blood) mainly made up of fibrin and fibronectin, and which will constitute a provisional matrix. This matrix fills the lesion partly and will allow the migration, within the injured zone, of inflammatory cells recruited to ensure the debridement of the wound. This phase is characterized by the infiltration on the site of the lesion, of many inflammatory cells (polynuclear, macrophages) ensuring the defense of the organization against possible foreign micro-organisms as well as the cleaning of the wound or debridement.

The second phase corresponds to the development of the granulation tissue. One observes initially a colonization of the wound by migration and proliferation of the fibroblasts. Then, the migration of endothelial cells starting from the healthy vessels will allow the neovascularization, or angiogenesis, of the injured tissue. In the granulation tissue, the fibroblasts are activated and will be differentiate into myofibroblasts that present important contractile properties. These properties are generated by the actin microfilaments that thus allow a contraction of the wound. These myofibroblasts play a main function in the formation and the contraction of granulation tissue which will lead to the healing of the lesion. There is then migration of the keratinocytes starting from the edges of the wound, leading to the rebuilding of the skin.

This phase of development of the granulation tissue is initiated following a preliminary reduction in the general inflammatory state of the lesion, with the progressive disappearance of polynuclear and the appearance of macrophages.

Nevertheless, certain types of wounds do not heal correctly, the 3 key stages of the process described previously turned in an abnormal way. Indeed the speed and the quality of the healing of a wound depend on intrinsic and extrinsic factors. This process of repair can thus be abnormally prolonged according to:
  etiology of the wound;
  its state and its localization;
  occurrence of an infection caused by the presence of certain infectious agent like *Staphylococcus aureus* or *Pseudomonas aeruginosa*; the existence of a preexistent pathology (like the diabetes, an immunizing deficiency, a venous insufficiency, etc);
  external environment; or genetic factors predisposing or not with disorders of the wound healing.

To enhance the process of wound healing, for both wounds which heal naturally and chronic wounds, it is known from the art to use phototherapy. Two types of phototherapies are known, the photodynamic therapy and the photobiomodulation.

Photodynamic therapy is a method that uses a photosensitizer, or photosensitizing agent, which is disposed or injected near skin or wound cells and activated by a light of a specific wavelength. Photosensitizers have the ability to interact with the nearby skin cells when exposed to a light with a specific wavelength. Photodynamic therapy is thus an indirect phototherapy because the light is provided to the photosensitizer to treat the skin cells, not directly to the skin cells.

Photobiomodulation is a method allowing to have a biological effect on skin or wound cells directly, which means without the need of any provisional product or composition to transpose or potentialize any biological effect engendered by the light source. This method can be distinguished from the photodynamic therapy which needs absolutely and every time the intervention of an intermediate product (photosensitizer or a photosensitizing agent) between the light source and the cells to potentialize the biological effect of the light on cells. In other words, in photobiomodulation, light has a direct effect on cells whereas, in photodynamic therapy, light has an indirect effect on cells via the activated photosensitizer. As mentioned in the technical field above, the present invention is directed to photobiomodulation.

Furthermore, in phototherapy, it is well known to determine the wavelength of the light to be provided depending on the type of effect that is expected on the skin cells. Particularly, light having a wavelength between 435 and 500 nm (blue light) has antibacterial effects and also act on human cells. [Ashkenazi H., Malik Z., Harth Y., Nitzan Y., Eradication of *Propionibacterium acnes* by its endogenous porphyrins after illumination with high intensity blue light. *FEMS Immunology and Medical Microbiology* 2003, 35:17-24].

More particularly, it was shown that blue light irradiation enables to inhibit the proliferation and migration of skin cells [Taflinski, L, Demir, E, Kauczok, J, Fuchs, P C, Born, M, Suschek, C V, Oplander, C: Blue light inhibits transforming growth factor-beta1-induced myofibroblast differentiation of human dermal fibroblasts. *Experimental dermatology* 2014, 23: 240-246] and [Mamalis A., Garcha M., Jagdeo J. Light Emitting Diode-Generated Blue Light Modulates Fibrosis Characteristics: Fibroblast Proliferation, Migration Speed, and Reactive Oxygen Species Generation Lasers in Surgery and *Medicine* 201547: 210-215]. It is also well known that inhibiting the proliferation of skin cells can be useful to enhance the phase of remodeling during wound healing.

As an example of the effect of blue light, document US-A-2014/0277293 is directed to the use of LED generated low-level light therapy. Tests show that light emitting diode having a dominant emission wavelength of 415 nm, wavelength comprised between 385 and 445 nm, and providing an effective fluence comprised between 0 and 35 J/cm$^2$ during many defined irradiation times which means that the irradiance of the light source used is of 43 mW/cm$^2$, allows to inhibit fibroblast proliferation. This document thus supports the fact that blue light emission is generally known as an inhibitor of the proliferation of specific types of skin cells.

It should be noted that toxicity occurs for shorter and dominant emission wavelengths of blue light between 410 and 420 nm [Oplander, C, Hidding, S, Werners, F B, Born, M, Pallua, N, Suschek, C V: Effects of blue light irradiation on human dermal fibroblasts. *Journal of photochemistry and photobiology B, Biology* 2011, 103: 118-125]. Therefore, the blue light emission with a dominant emission wavelength of 415 nm disclosed in the method of US-A-2014/0277293 might be toxic.

SUMMARY OF THE INVENTION

It was surprisingly discovered that irradiating cells with blue light under specific conditions can have an unexpected technical effect consisting in promoting or inducing growth and proliferation of irradiated cells. Indeed, this is particularly unexpected because blue light is generally known for anti-proliferation effect whereas these experimentations showed that blue irradiation under specific conditions enables to have proliferation effect, preferably at specific dominant emission wavelength, irradiance and/or fluence.

Proliferation effect is particularly advantageous to enhance the phase of proliferation during wound healing. Indeed, inducing a proliferation effect during the phase of proliferation and granulation is the key to enhance the wound healing process.

Furthermore, irradiating cells of a wound with blue light enables to benefit from all the known effects of blue light, such as antibacterial and anti-inflammatory effects, in addition to the unexpected proliferation effect.

The unexpected technical effect is achieved with a light source device comprising a light emitting element for emitting a blue light having a wavelength ranging from 435 to 500 nm, the light source device being configured to provide the blue light to at least one cell (C) at a transmitted fluence ranging from 0.01 to 18.5 J/cm$^2$ to promote or induce growth and proliferation of the cell (C) and wherein the light emitting element (12) has a power density ranging from 0.05 to 30 mW/cm$^2$.

According to an embodiment of the light source device, the cell is selected from a skin cell.

According to another embodiment, skin cells are keratinocytes or fibroblasts.

According to another embodiment, the dominant emission wavelength ranges from 450 to 490 nm, more particularly from 450 to 460 nm.

According to another embodiment, the light source device is configured to provide the blue light at a transmitted fluence so that the cell receives an effective fluence ranging from 0.01 to 10 J/cm$^2$.

According to another embodiment, the light emitting element has a power density ranging from 20 to 25 mW/cm$^2$, and preferably of 23 mW/cm$^2$.

According to another embodiment, said light emitting element comprises at least one LED.

According to another embodiment, the light source device comprises a power source providing electrical power to said light emitting element.

According to another embodiment, said power source is a battery.

According to another embodiment, the light source device comprises at least one among a microchip processor, a control unit, a communication unit, an external port and a sensor.

It is another object of the invention to provide a light source assembly comprising a product adapted to be in contact with the skin or a wound and a light source device as described above connected to the product for providing blue light to at least one skin cell, preferably of the wound.

According to an embodiment of the light source assembly, the product is one among a dressing, a strip, a compression means, a band-aid, a patch, a gel, a film-forming composition and a rigid or flexible support, preferably a dressing.

According to another embodiment, the dressing comprises at least a hydrocolloid or an adhesive layer in contact with the skin or the wound.

According to another embodiment, the light source assembly is adapted to dispose the light emitting element in a position wherein the light emitting element is facing the skin, preferably facing a wound formed on the skin.

DETAILED DESCRIPTION

The present invention will be described below relative to several specific embodiments. Those skilled in the art will appreciate that the present invention may be implemented in a number of different applications and embodiments and is not specifically limited in its application to the particular embodiment depicted herein.

For the purpose of the present invention, the following terms are defined.

The term "Wavelength" is the distance between two peaks of a wave. The symbol for wavelength is λ (lambda) and the unit of measurement is nanometers (nm).

The term "Dominant emission wavelength" is the wavelength or a narrow range of wavelengths the light source emits the majority of the time. The term "power" refers to the rate at which work is perform; the unit of power is Watt (W) and since the light output power is low it is expressed in milliwatts (mW).

The term "power density" or "light intensity", or "irradiance", or "exitance" is the power divided by the area of the target being illuminated by the light and is expressed in mW/cm$^2$.

The term "fluence" or "energy density" or "dose" expressed in Joules per cm$^2$ (J/cm$^2$) is the product of power (mW) and time per spot size (cm$^2$).

The term "photobiomodulation" is the ability of the light source device to have a biological effect on cells, in particular on skin cells, directly, which means without the need of any provisional product or composition to transpose or potentialize any biological effect engendered by the light source. This term can be distinguished from the term of "photodynamic therapy" which needs absolutely and every time the intervention of an intermediate product between the light source and the cells to potentialize the biological effect of the light on cells.

A first object of the invention is a light source device comprising a light emitting element for emitting a blue light having a wavelength ranging from 435 to 500 nm, the light source device being configured to provide the blue light to at least one cell (C) at a transmitted fluence ranging from 0.01 to 18.5 J/cm$^2$ to promote or induce growth and proliferation of the cell (C) and wherein the light emitting element (12) has a power density ranging from 0.05 to 30 mW/cm$^2$.

Figure 1:
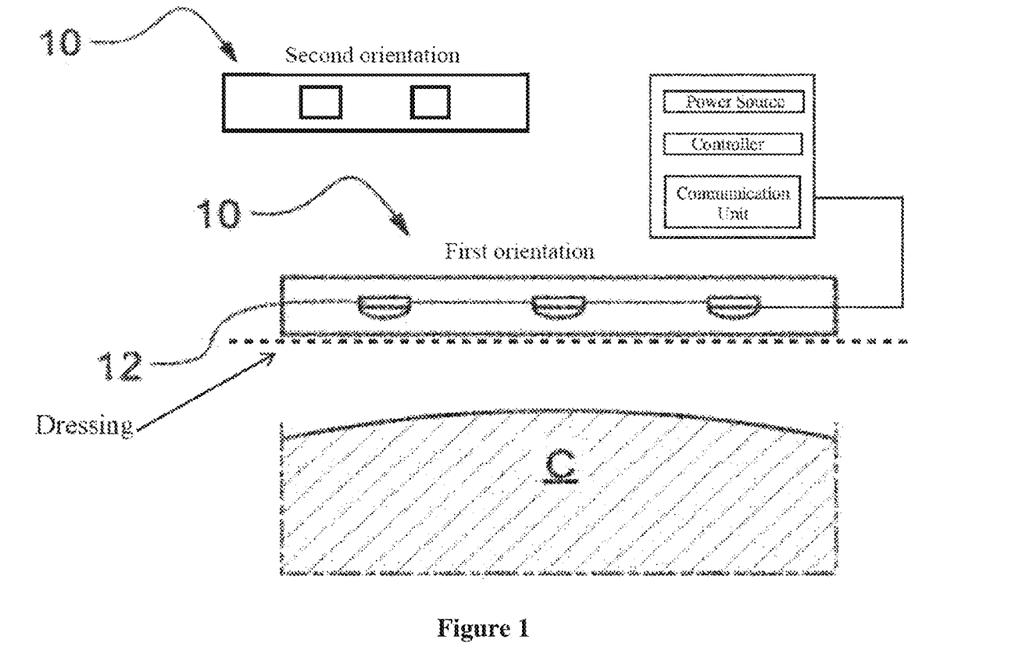
FIG. 1 represents in a cross section view an embodiment of a photobiomodulation device used in the treatment of various skin conditions or for promoting or inducing growth and proliferation of cells in vitro or in vivo.

According to FIG. 1, a light source device 10 comprising a light emitting element 12 for emitting a blue light having a wavelength ranging from 435 to 500 nm is proposed. The light source device 10 is able to emit light at wavelengths within the range of 435 to 500 nm, preferably within a specific dominant emission wavelength of 450-490 nm and preferably within a specific dominant emission wavelength of 450-460 nm. More particularly, the chosen dominant emission wavelength may be 453 nm. It should be noted that emitting light at wavelengths within the range of 435 to 500 nm allows blue light emission not to be toxic, contrary to the chosen blue light wavelength range of US-A-2014/0277293, because of most of the emitted wavelengths are comprised in another dominant emission wavelength.

Furthermore, the light source device 10 is configured to provide blue light to cells C at an irradiance and a fluence (dose or energy density) able to promote or induce growth and proliferation of cells C. The fluence at which blue light is provided to the cells C corresponds to the specific conditions, particularly specific condition of irradiance and exposition with a light source having a specific dominant emission wavelength: allowing to obtain the unexpected technical effect with regard to the prior art, such as US-A-2014/0277293. Indeed, it was observed that monitoring the irradiance of the provided blue light allows to have proliferation effect so that growth and proliferation of irradiated cells are promoted or induced. Particularly, it was observed that blue light irradiation have a proliferation effect on keratinocytes and fibroblasts.

It seems that the key notions of dominant emission wavelength and/or irradiance give a particular benefit to the unexpected proliferative effect on keratinocytes and fibroblasts from skin wound.

Experimentation showed that proliferation effect may be obtained thanks to the action of blue light irradiation on cell pathways. Indeed, it was observed that providing the cells C with blue light induces a downregulation or an upregulation of different pathways. Particularly, the TGF-BETA signaling pathway (KEGGID: 4350) is downregulated. This pathway leads to the differentiation of fibroblasts. Therefore, reducing fibroblast's differentiation explain the activation of the proliferation (because the 2 functions are opposite in cells behavior). On the contrary, ErbB signaling pathway is activated, explaining the increase of the fibroblast, as EGF has been linked to their proliferation. [Yu et al. Effect of EGF and bFGF on fibroblast proliferation and angiogenic cytokine production from cultured dermal substitutes. J Biomater Sci Polym Ed. 2012; 23(10):1315-24].

The growth and proliferation of cells, preferably skin cells, may be performed in vitro or in vivo. Indeed, cells may be in culture or may be cells of a tissue, preferably a mammal tissue.

The light source device 10 may be configured to provide light at a specific fluence to a mammal skin tissue or to in vitro cells to provide the proliferation effect. Thus, the light source device 10 is particularly useful in wound healing. According to this embodiment, the light source device transmits the blue light onto the surface of a wound.

Depending on many interference means, as described above, disposed between the cells and the light source, the effective fluence of the blue light received by the skin cells may be lower than the fluence transmitted by the light emitting element. Indeed, it was also observed that a larger fluence has to be generally transmitted by the light emitting element 12 to provide a predetermined fluence of blue light to skin cells C, i.e. an effective fluence of blue light adsorbed by cells. Indeed, during the emission, a part of the blue light is adsorbed by other elements than skin cells C which induces a loss of blue light. Therefore, the light source device 10 is configured to provide blue light at a transmitted fluence so that the skin cells C receive a predetermined fluence or an effective fluence. Depending on the elements that can be present between the light emitting element and the target cells, the attenuation or absorption effect of the light may lead to an attenuation ranging from 20% to 60% or from 30% to 50% of the energy density, particularly around 45%.

To obtain the unexpected proliferation effect with skin cells, preferably with keratinocytes, the irradiance or power density is in the range of about 0.05 mW/cm$^2$ to about 30 mW/cm$^2$, particularly 0.1 mW/cm$^2$ to 1 mW/cm$^2$, 1 mW/cm$^2$ to about 2 mW/cm$^2$, 2 mW/cm$^2$ to 5 mW/cm$^2$, 5 mW/cm$^2$ to 10 mW/cm$^2$, 15 mW/cm$^2$ to 25 mW/cm$^2$ or any irradiance in a range bounded by, or between, any of these values. The power density used to treat target cells or target tissue is of 0.05 to 30 mW/cm$^2$, preferably of 15 to 25 mW/cm$^2$, preferably of 20 to 25 mW/cm$^2$ and more particularly of 23 mW/cm$^2$.

The effective dose or fluence received by skin cells, in particular of a wound or a given surface of skin tissue, may be about 0.01 J/cm$^2$ to about 0.1 J/cm$^2$, or about 0.1 J/cm$^2$ to about 10 J/cm$^2$, or about 1 J/cm$^2$ to about 2 J/cm$^2$, or about 2 J/cm$^2$ to about 3 J/cm$^2$, about 3 J/cm$^2$ to about 4 J/cm$^2$, or about 4 J/cm$^2$ to about 5 J/cm$^2$, or about 5 J/cm$^2$ to about 6 J/cm$^2$, or about 6 J/cm$^2$ to about 7 J/cm$^2$, or about 7 J/cm$^2$ to about 8 J/cm$^2$, or about 8 J/cm$^2$ to about 9 J/cm$^2$, or about 9 J/cm$^2$ to about 10 J/cm$^2$, or any light dose in a range bounded by, or between, any of these values. Preferably, the effective fluence used to treat target cells or target skin tissue is of about 0.01 J/cm$^2$ to about 10 J/cm$^2$.

As indicated above, the fluence (dose or energy density) notably depends on both irradiance (mW/cm$^2$) and time. Therefore, obtaining the predetermined fluence may be accomplished by using a higher power light source, which may provide the needed energy in a shorter period of time, or a lower power light source may be used for a longer period of time. Thus, a longer exposure to the light may allow a lower power light source to be used, while a higher power light source may allow the treatment to be done in a shorter time.

The duration of radiation or light exposure administered to a skin tissue or a culture of skin cells, such as keratinocytes, may also vary. In some embodiments, the exposure ranges from at least 1 second, at least few seconds, or at least 1 minute, or at least 2, 3, 4, 5, 6, 7, 8, 9, 10, 11, 12, 13, 14, 15, 16, 17, 18, 19, 20 minutes; or up to about 1 hour or, for any amount of time in a range bounded by, or between, any of these values.

According to a specific embodiment, the light source device is used in the growth and proliferation of dermis cells, in particular of fibroblasts under specific conditions. Particularly, it was observed that proliferation effect occurs on fibroblasts when provided with an effective fluence of about 6 J/cm$^2$ with a power density of about 23 mW/cm$^2$ during about 7.5 minutes. Similarly, it was observed that proliferation effect occurs on keratinocytes when provided with an effective fluence of about 1 to 10 J/cm$^2$ with a power density of about 23 mW/cm$^2$ during about 7.5 minutes For thermal issues, light source device may be configured to irradiate cells either continuously or in pulses. Indeed, pulsed light irradiation will typically be preferred than continuous light if there are some thermal issues; indeed, light source provides heating. The decision whether to use constant irradiation of pulsed light irradiation depends on the exact application and on the total desired irradiation. When the light exposure depends on the duration of a pulsed light, the net light time may be determined by the sum of the duration of each pulse.

The light emitting element 12 is a device able to perform photobiomodulation. An example of such a light emitting element 12 is a light-emitting diode (LED or OLED, preferably LED) or a lamp which is able to emit light at wavelengths within the ranges of 435 to 500 nm and having preferably a dominant emission wavelength comprised between 450-460 nm, as well as at a dominant emission wavelength of 453 nm. In the embodiment shown on FIG. 1, the light emitting element 12 comprises three light-emitting diodes. Alternatively, the light emitting element 12 may comprise one or more light-emitting diode (or lamp) able to emit a blue light having a wavelength ranging from 435 to 500 nm, having preferably a dominant emission wavelength comprised between 450 to 460 nm or having a dominant emission wavelength of about 453 nm.

For supplying electricity to the light emitting element 12, the light source device 10 may comprise a power source connected to the light emitting element 12. The power source may comprise an electric cable to connect to a power grid. Alternatively, the power source may be a battery. The light source device 10 is compact and able to communicate with a smartphone or a tablet thanks to a wireless communication protocol (Bluetooth or Bluetooth smart or Bluetooth Low Energy, preferably Bluetooth Low Energy).

For controlling the light emitting element 12, the light source device 10 may comprise at least one among a LED Driver, a sensor, a microchip processor, a control unit, a communication unit and an external port, an antenna, a memory.

A sensor may allow the light source device 10 to measure parameters of the wound healing. These parameters may be for example the temperature and the oxygenation level of the wound.

The microchip processor or the control unit may allow the light source device 10 to monitor the supply of electricity to the light emitting element 12 to guarantee an optimum or desired blue light exposure. For example, the microchip processor or the control unit may control whether the light exposure is continuous or in pulses as well as the frequency and the duration of the pulses depending on predetermined parameters or live parameters such as values measured by a sensor of the light source device 10.

Furthermore, a communication unit may allow a user to recover data from or transmit data to the light source device 10. For example, data may be transmitted to a smartphone or any other external device, notably an external device comprising a screen to display information useful to the user. The communication unit may be configured for wireless transmission or wired communication. In the case of a wired communication, the light source device 10 may comprise an external port connected to the communication unit for data transmission. Alternatively, the communication unit may be configured for both wireless and wired communication.

Moreover, the light source device 10 may be included in a light source assembly (not shown) which comprises a product adapted to be in contact with the skin or a wound formed on the skin. In this case, the light source device 10 is connected to the product for providing blue light to at least one skin cell of the skin or the wound.

For improving blue light effect, the light source assembly may be adapted to dispose the light emitting element 12 in a position wherein the light emitting element 12 is facing the skin, preferably facing a wound formed on the skin. In other words, the light source assembly is also adapted to place the light emitting element on the facing page of the skin, preferably of the wound.

Furthermore, the light source device 10 may be configured so that blue light is irradiated to the skin cells or the wound through the product. In doing so, the light source device 10 can irradiate the skin cells or the wound without direct contact.

The light source assembly may be configured to allow setting or predetermining of the distance between the light emitting element 12 and the skin. Indeed, light intensity decreases with the square of the distance from the source of the light. For example, light 1 meter away from a source is four times as intense as light 2 meters from the same source. Therefore, setting the distance between the light emitting element 12 and the skin allows to monitor the irradiance and thus the fluence provided to the skin cells. The distance between the light emitting element 12 and the skin may be predetermined from 0 to 50 mm, and preferably 0 to 20 mm in the case of a wound dressing for example. The distance between the light emitting element 12 and the skin may be of several centimeters in the case of a lamp used alone for example.

For setting or predetermining the distance between the light emitting element 12 and the skin, the dimension of the product may be chosen to predetermine or set the distance between the light emitting element 12 and the skin cells. Alternatively or in combination, the light source assembly may further comprise an adjustable element for adjusting the distance between the light emitting element 12 and the skin.

The light source device 10 may also be configured so that the light emitting element 12 may be selectively orientated to better target the skin cells to be irradiated. This orientation, or homogenization of the light emitting element 12 allows the irradiation to be more adapted to the geometry and the characteristics of a wound. These advantages become even more significant when the light source device 10 comprises a plurality of light emitting elements 12. In this case, the light emitting elements 12 may be orientated independently from each other to widen the irradiated area.

Furthermore, the light source device 10 may comprise a lens for focusing the light onto the target cells or tissue to make the irradiation more precise.

The product may be one among a dressing, a strip, a compression means, a band-aid, a patch, a gel and a rigid or flexible support, a film-forming composition or similar. Furthermore, in an embodiment of the light source assembly, the product may be arranged so that the light emitting element 12 is disposed on the interior of the product or in its inferior or superior surface. In this embodiment, the product adapted to contact the skin or a wound is preferably a dressing. The dressing may comprise at least a hydrocolloid or an adhesive layer in contact with the skin or the wound.

The light source assembly may be of any size or shape. In one particular embodiment, the assembly may be 8×8 cm in size. In another embodiment, the assembly may be 4×4 cm in size. The product may comprise an interior layer comprising a mesh material and a tissue gel. The mesh material allows exudate from a wound to which the dressing is applied to be absorbed into the dressing whilst allowing the tissue gel to flow through it so that it can be absorbed by a wound being treated.

For allowing the light source assembly to be reusable while avoiding repetitive cleanup, the product may be disposable and interchangeable. In other words, the product may be configured to be separated from the light source device 10 so that a same light source device 10 can be used several times without the need of a cleanup. It also allows to change the electronic elements included in the light source device 10 for maintenance, for example for recharging the battery.

Moreover, the effect of irradiation may at times be enhanced by the addition of photosensitizer substances to the target cells or tissue. The concentration of such substance is substantially lower than concentrations used in photodynamic therapy. For example, a culture of skin cells, such as fibroblasts or keratinocytes, may be supplemented with small amounts of a photosensitizer substance, such as hematoporphyrin derivatives prior to light irradiation. Such substances may also be applied topically onto the skin prior to the light therapy.

A method for inducing or promoting growth and proliferation of cells is also proposed. The method may be performed by any light source device but preferably by the light source device 10 and the light source assembly described above.

Cells or tissue are irradiated with a light at wavelengths between 435 to 500 nm, and preferably having a dominant emission wavelength comprised between 450 and 460 nm. More particularly, the chosen dominant emission wavelength may be of 453 nm. The method may be performed in vivo or in vitro. Cells or tissue may be in culture or directly from a mammal tissue.

For inducing or promoting growth and proliferation of cells, cells or tissue may be irradiated to receive an effective fluence comprised between 0.01 and 10 J/cm$^2$.

For inducing or promoting growth and proliferation of cells also, light emitting source used in this method is in the range of about 0.05 mW/cm$^2$ to about 30 mW/cm$^2$, particularly 0.1 mW/cm$^2$ to 1 mW/cm$^2$, 1 mW/cm$^2$ to about 2 mW/cm$^2$, 2 mW/cm$^2$ to 5 mW/cm$^2$, 5 mW/cm$^2$ to 10 mW/cm$^2$, 15 mW/cm$^2$ to 25 mW/cm$^2$ or any irradiance in a range bounded by, or between, any of these values. Preferably, the power density used to treat target cells or target tissue is of 0.05 to 30 mW/cm$^2$, preferably of 15 to 25 mW/cm$^2$, preferably of 20 to 25 mW/cm$^2$ and more particularly of 23 mW/cm$^2$.

More generally, the irradiation of blue light performed in this method may be set using all the different values of fluence, power intensity and time described above for the light source device 10 and the light source assembly.

This method allows to benefit from the same effects as described above for the light source device 10 and the light source assembly. Particularly, the present method allows to obtain the unexpected technical effect of blue light consisting in inducing or promoting growth and proliferation of cells or tissue. In particular, the method according to the invention is very useful for growth and proliferation of skin cells, such as cells of epidermis and/or dermis, such as keratinocytes or fibroblasts, preferably keratinocytes.

The present invention also describes a light source device for use for the in vivo growth and proliferation of cells or tissue, preferably skin cells or tissue, such as keratinocytes or fibroblasts. Preferably, the light source device is according to the present invention.

The present invention also describes a light source assembly containing a light source device for use for the in vivo growth and proliferation of cells or tissue, preferably skin cells or tissue, such as keratinocytes or fibroblasts. Preferably, the light source assembly is according to the present invention. The invention will be illustrated further by the following examples:

Example 1: Effect of the Blue Light on the Growth and Proliferation of Keratinocytes Cell Culture Keratinocytes (HaCaT, Immortal Human Keratinocyte in Dulbecco's Modified Eagle Medium, from CLS Company) were incubated in 96 multi-well plates.

The concentration of cells was about 2.5×10$^4$ cells/well. 48 hours after cell incubation, cells were washed with a phosphate buffered saline (PBS) solution.

Then, the wells containing the keratinocyte cells are treated by a blue light.

Light Treatment

For the light treatment Lumileds Luxeon Rebel LXML-PR01-0275 from Koninklijke Philips N.V. (Eindhoven/Netherlands) was used. The plates were irradiated from a distance of 5 cm with a power density of 23 mW/cm$^2$. The beam divergence was ±15° with a dominant emission wavelength of 453 nm (blue light).

The keratinocyte wells were irradiated with different energy densities.

XTT Test (Measurement of the Keratinocyte Cell Proliferation)

The XTT Cell proliferation test is a well-known method for the skilled person. For this test the Colorimetric Cell Viability Kit III from PromoKine (Heidelberg/Germany) was used. For the test 50 μL of labeling-mixture containing labeling reagent and electron coupling reagent was mixed with cell suspension where the XTT (2,3-bis(2-methoxy-4-nitro-5-sulfophenyl)-2H-tetrazolium-5-carboxanilide) is metabolized to water soluble formazan dye. Only viable cells have the ability to metabolize, hence the formazan is used to directly quantify the proliferation measured by spectrophotometric absorption with Infinite® 200 PRO microplate reader from Tecan Group AG. (Männedorf/Switzerland).

Results

Figure 2:
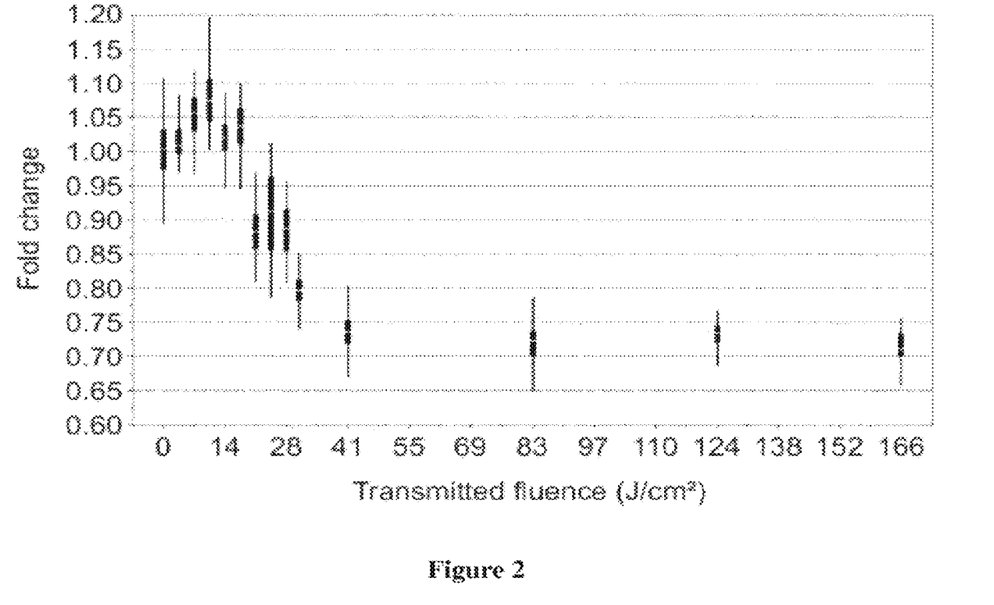
FIG. 2 is a schematic representation showing the keratinocyte proliferation, 24 hours after different energy densities with blue light irradiation (transmitted fluence in J/cm$^2$).

The cell proliferation of keratinocytes is illustrated in the graph of FIG. 2. The graph represents the "fold change" in function of the transmitted fluence with blue light irradiation to the cells.

By "fold change", it means the ratio of proliferation with blue light on the proliferation with non-irradiated cells In order to evaluate the attenuation or absorption of the light that can occur if the skin tissue is irradiated with blue light, the loss of light power has been evaluated through a lid (which reflects the light), a plate (culture wells which absorbs the light) and a medium culture (4 mm of height for a volume of about 1.5 mL).

The energy density (fluence) effectively received after passing through the different elements listed above (lid, plate and medium culture) was measured with a Power Meter® 843-R-USB from Newport Corporation. A loss of 45% has been observed.

Figure 3:
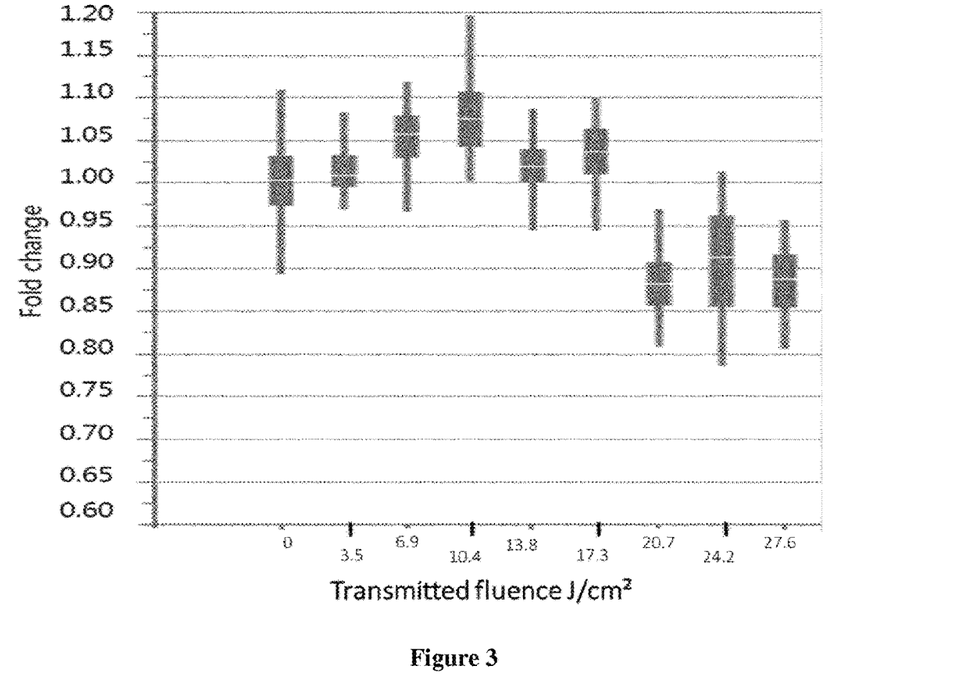
FIG. 3 is a zoom of FIG. 2 in the transmitted fluence range of 0.01 to 30 J/cm$^2$.

The graph of FIG. 2 and the zoom of FIG. 3 shows that the exposure of keratinocytes to blue light (453 nm) with energy densities of less than 18.5 J/cm$^2$, promotes or induces proliferation of keratinocytes which well shows that an irradiation with blue light can be used for the treatment of wounds and injuries. On the contrary, the exposure of keratinocytes to blue light (453 nm) with energy densities higher than 18.5 J/cm$^2$ inhibits proliferation of keratinocytes which and would therefore not be suitable for the closure of wounds and injuries.

Example 2: Effect of the Blue Light on the Growth and Proliferation of Fibroblasts The same protocol as the one used in example 1 was used by replacing the keratinocyte cells by fibroblast cells: Normal Human Dermal Fibroblast (NHDF) in Dulbecco's Modified Eagle Medium (available from PromoCell Company).

Figure 4:
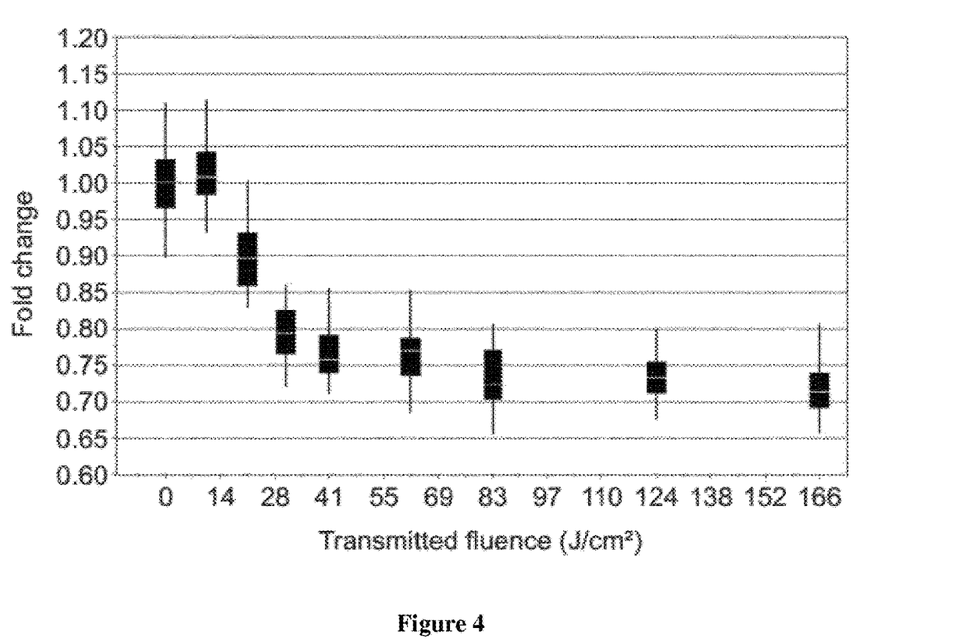
FIG. 4 is a schematic representation showing the fibroblast proliferation, 24 hours after different energy densities with blue light irradiation (transmitted fluence in J/cm$^2$).

The cell proliferation of fibroblasts is illustrated in the graph of FIG. 4. The graph represents the "fold change" in function of the transmitted fluence with blue light irradiation to the cells.

The graph of FIG. 4 shows that the exposure of fibroblasts to blue light (453 nm) with energy densities of less than 18.5 J/cm$^2$ promotes or induces proliferation of fibroblasts which well shows that an irradiation with blue light can be used for the treatment of wounds and injuries. On the contrary, the exposure of fibroblasts to blue light (453 nm) with energy densities higher than 18.5 J/cm$^2$ inhibits proliferation of fibroblasts which and would therefore not be suitable for the closure of wounds and injuries.

The invention claimed is:

1. A method for inducing or promoting growth and proliferation of at least one cell of keratinocytes or fibroblasts, the method comprising the steps of:
   causing the at least one cell to be illuminated by operation of a light source device configured to induce or promote growth and proliferation of the at least one cell, wherein the light source device is configured to emit only blue light, and wherein the light source device comprises:
   a light emitting element configured to only emit a blue light having a wavelength ranging from 435 to 500 nm and oriented to target the at least one cell of keratinocytes or fibroblasts,
   the light source device being configured to provide the blue light at transmitted fluence ranging from 0.01 to 18.5 J/cm$^2$,
   wherein the light emitting element has a power density ranging from 0.05 to 30 mW/cm$^2$
   wherein the light source device is configured so that the light emitting element is selectively orientated to target the skin cells to be irradiated, and
   wherein an output of the light emitting element is configurable between a first orientation and a second orientation having a different geometry of the output than in the first orientation, such that the irradiation is adaptable to a geometry and characteristics of a wound.

2. The method of claim 1, wherein the emission wavelength of the light emitting element ranges from 450 to 490 nm, more particularly from 450 to 460 nm.

3. The method of claim 1, wherein the light source device is configured to provide the blue light at transmitted fluence so that the at least one cell receives the effective fluence ranging from 0.01 to 10 J/cm$^2$.

4. The method of claim 1, wherein the light emitting element has a power density ranging from 20 to 25 mW/cm$^2$.

5. The method of claim 1, wherein said light emitting element comprises at least one LED.

6. The method of claim 1, further comprising a power source providing electrical power to said light emitting element.

7. The method of claim 6, wherein said power source is a battery.

8. The method of claim 1, further comprising at least one among a microchip processor, a control unit, a communication unit, an external port and a sensor.

9. A method for inducing or promoting growth and proliferation of at least one cell of keratinocytes or fibroblasts, the method comprising the following steps:
   providing a product adapted to be in contact with skin or a wound of a patient;
   adapting a light source device connected to the product for providing blue light to the at least one cell;
   causing the at least one cell to be illuminated by operation of a light source device configured to induce or promote growth and proliferation of the at least one cell, wherein the light source device is configured to emit only blue light, and wherein the light source device comprises:
   a light emitting element configured to only emit a blue light having a wavelength ranging from 435 to 500 nm and oriented to target the at least one cell of keratinocytes or fibroblasts,
   the light source device being configured to provide the blue light at a transmitted fluence ranging from 0.01 to 18.5 J/cm$^2$,
   wherein the light emitting element has a power density ranging from 0.05 to 30 mW/cm$^2$,
   wherein the light source device is configured so that the light emitting element is selectively orientated to target the skin cells to be irradiated, and
   wherein an output of the light emitting element is configurable between a first orientation and a second orientation having a different geometry of the output than in the first orientation, such that the irradiation is adaptable to a geometry and characteristics of a wound.

10. The method of claim 9, wherein the at least one cell is one cell of the wound.

11. The method of claim 9, wherein the product is one among a dressing, a strip, a compression means, a band-aid, a patch, a gel, a film-forming composition and a rigid or flexible support.

12. The method of claim 9, wherein the product adapted to be in contact with skin or a wound of a patient is a dressing, and wherein the dressing comprises at least a hydrocolloid or an adhesive layer in contact with the skin or the wound.

13. The method of claim 9, wherein the light source assembly is adapted to dispose the light emitting element in a position wherein the light emitting element is facing the skin or a wound formed on the skin.

14. A method comprising:
    providing at least one cell of keratinocytes or fibroblasts in vivo or in vitro;
    inducing or promoting growth and proliferation of the at least one cell of keratinocytes or fibroblasts;
    wherein inducing or promoting growth and proliferation of the at least one cell comprises causing the at least one cell to be illuminated by operation of a light source device configured to induce or promote growth and proliferation of the at least one cell, wherein the light source device is configured to emit only blue light,
    wherein the light source device comprises a light emitting element configured to only emit a blue light having a wavelength ranging from 435 to 500 nm oriented to target the at least one cell of keratinocytes or fibroblasts, the light source device being configured to provide the blue light at a transmitted fluence ranging from 0.01 to 18.5 $J/m^2$, and
    wherein the light emitting element has a power density ranging from 0.05 to 30 $mW/cm^2$.

* * * * *